United States Patent [19]

Collins

[11] 4,002,072
[45] Jan. 11, 1977

[54] DEVICE AND METHOD OF OBTAINING A SAMPLE OF LIQUID

[76] Inventor: William J. Collins, 7005 Madison St., Merrillville, Ind. 46410

[22] Filed: Mar. 31, 1975

[21] Appl. No.: 563,590

[52] U.S. Cl. .............................. 73/425.6; 73/DIG. 9
[51] Int. Cl.² ......................................... G01N 1/12
[58] Field of Search ................. 73/DIG. 9, 425.4 R

[56] References Cited
UNITED STATES PATENTS

| 3,315,529 | 4/1967 | Feichtinger | 73/DIG. 9 |
|---|---|---|---|
| 3,455,164 | 7/1969 | Boyle | 73/DIG. 9 |
| 3,552,214 | 1/1971 | Collins | 73/DIG. 9 |
| 3,559,452 | 2/1971 | Perbix | 73/DIG. 9 |
| 3,751,986 | 8/1973 | Boron | 73/DIG. 9 |
| 3,805,621 | 4/1974 | Falk | 73/DIG. 9 |
| 3,859,857 | 1/1975 | Falk | 73/DIG. 9 |
| 3,877,309 | 4/1975 | Hance | 73/DIG. 9 |

*Primary Examiner*—S. Clement Swisher

[57] ABSTRACT

The invention involves providing a unique device and method of obtaining a sample of liquid, such as molten metal, preferably from a stream thereof. The device embodies improvements with respect to structural characteristics and dimensional factors with regard to components through which the liquid flows, including the disposition and use of buffer means and/or deoxidizing means in the flow path of the liquid.

21 Claims, 21 Drawing Figures

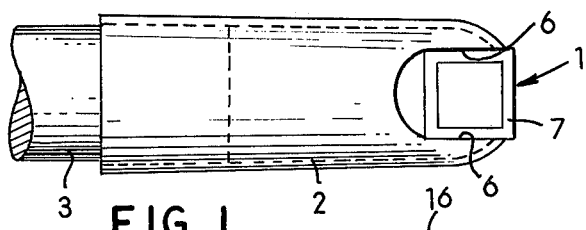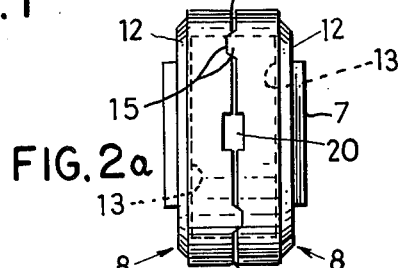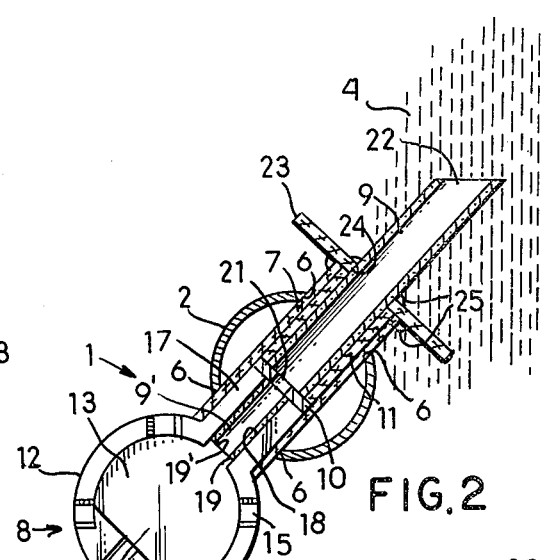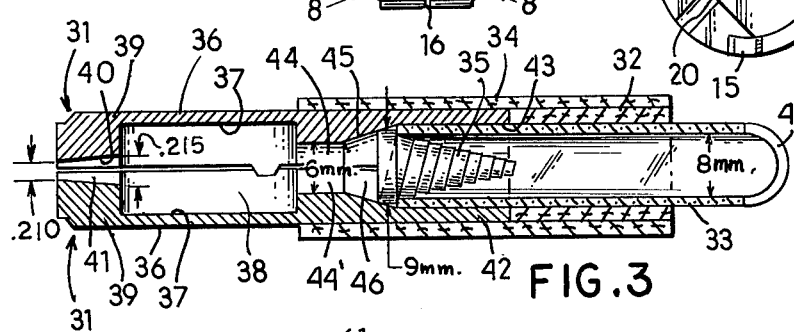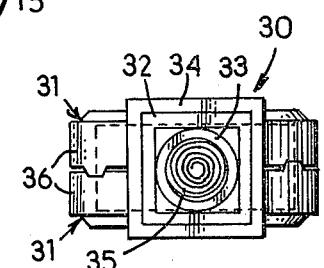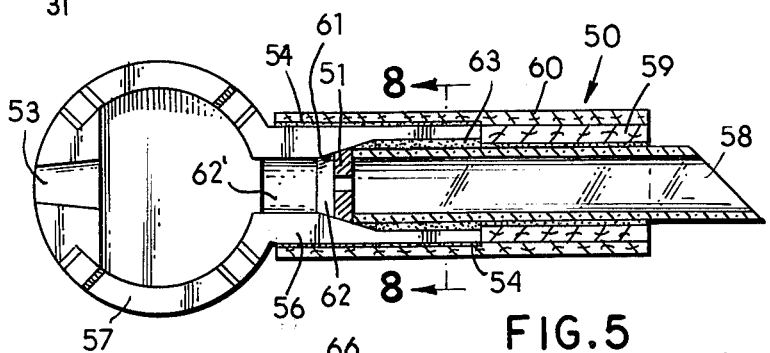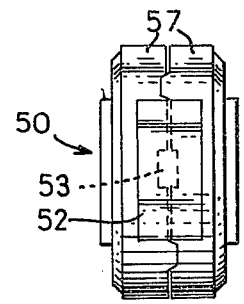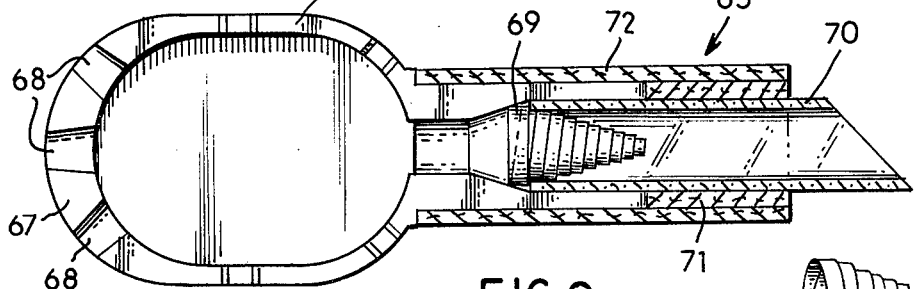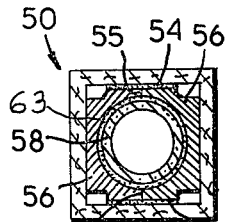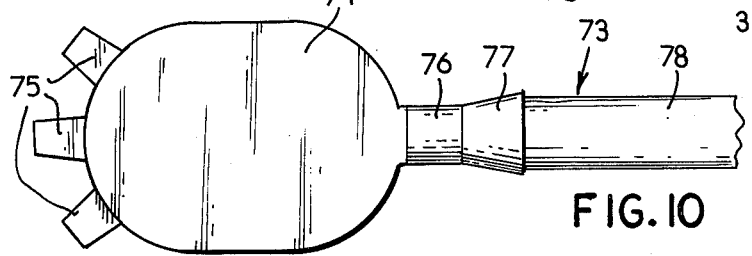

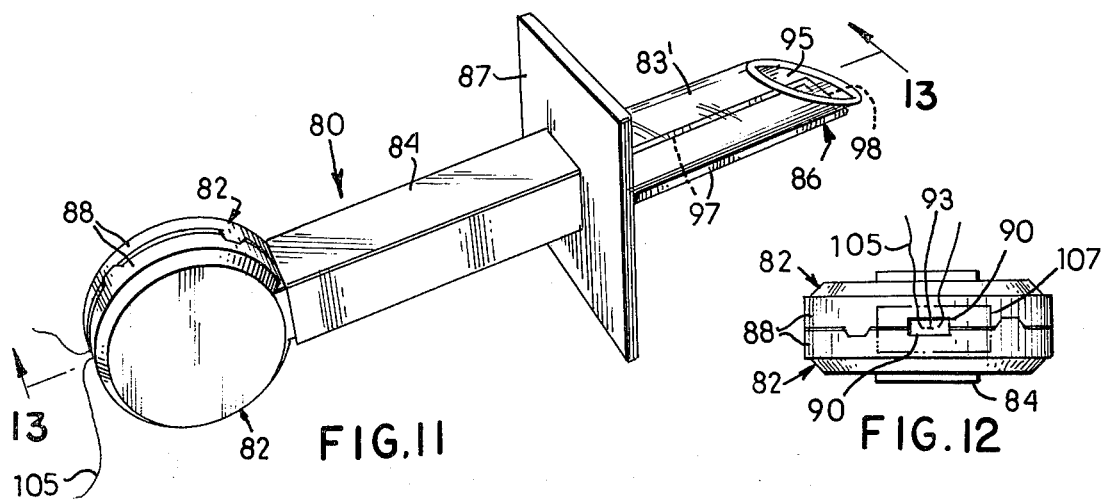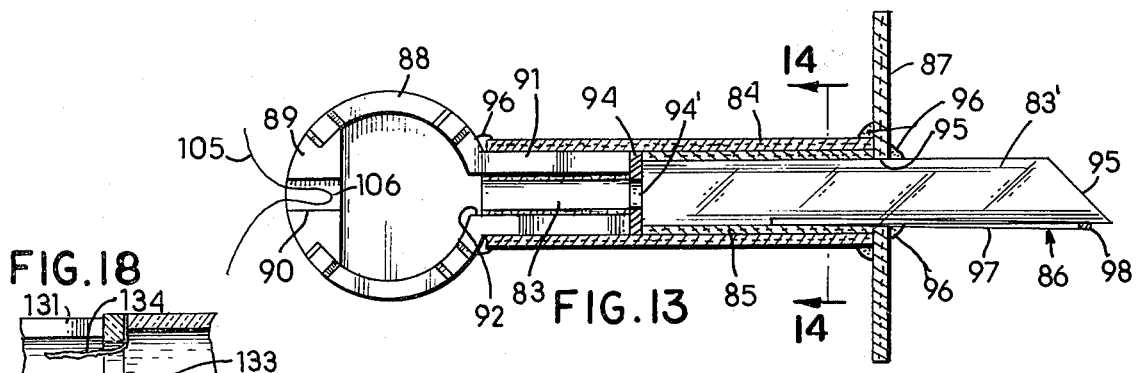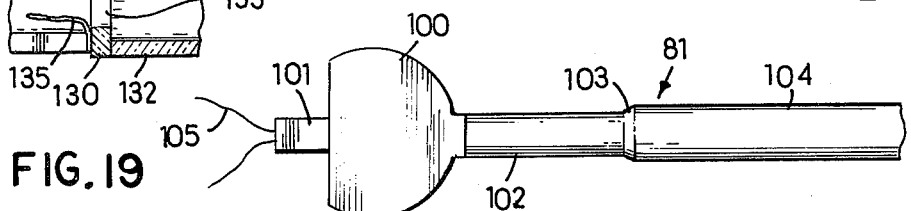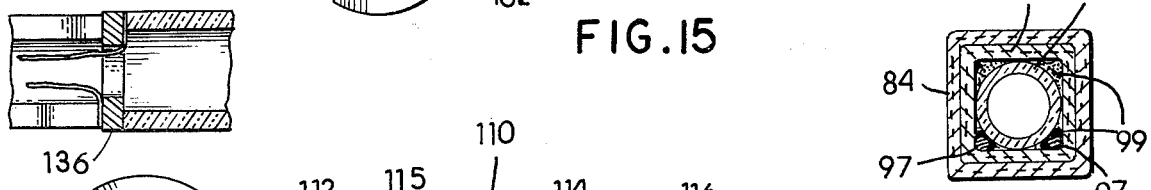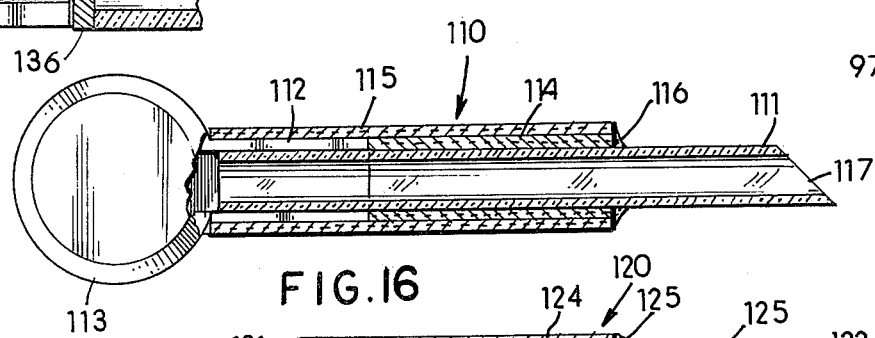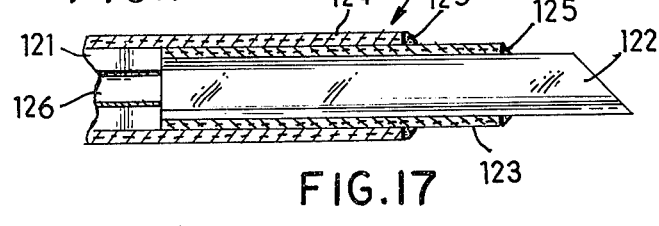

DEVICE AND METHOD OF OBTAINING A SAMPLE OF LIQUID

BACKGROUND OF INVENTION

The various devices disclosed in the subject application preferably comprise, among other things, a pair of half sections which form a primary chamber for receiving molten metal and tubular means or tube, preferably of Pyrex or other suitable heat resistant material, which has an inner extremity held in relation to the primary chamber by the half sections and an outer extremity provided with an entrance or inlet for initially receiving molten metal for flow through the tubular means into the primary chamber.

The peripheral and/or end contact or area of engagement between the inner end or extremity of the tubular means and portions of the half sections is such that the tubular means upon introduction into a stream of molten metal is subjected to appreciable shock throughout its entire length and this is transmitted to the aforesaid area and in order to reduce this shock factor and alleviate cracking or breakage of the tubular means, a buffer or shock absorbing means is interposed between the inner extremity of the tubular means and chamber.

More particularly, for example, if a killed grade of molten steel is being sampled the buffer means may be inert or of a nonchemical character so as to act only as a protective element between the tubular means and half sections. In the event, the grade of steel requires deoxidizing, then the buffer means may also be of pyrophoric character, such as aluminum, so that the means interposed between the inner extremity of the tubular means and the half sections serve both as a buffer or shock absorber, and as a deoxidizer. The deoxidizing means is so located that it is completely melted and diffused by and into the molten metal for conditioning the latter prior to its flow into the primary chamber.

In view of the foregoing, one of the important objects of the subject invention is to provide a device comprising a receiving means preferably composed of a pair of half sections forming a tubular formation and a primary chamber for receiving a sample of molten metal, including tubular means having an inner extremity disposed in relation to the tubular formation and an outer extremity provided with an entrance for initially receiving molten metal for flow through the tubular means into the chamber, and buffer means interposed between the inner extremity of the tubular means and chamber whereby to reduce the shock factor caused by the hot metal flowing into the device.

A significant objective of the invention is to provide a device in which the buffer means may be in the form of heat resistant material or in the form of a deoxidizing means or both. Otherwise expressed, a buffer means may also constitute a deoxidizing means and vice versa.

A specific object is to provide a setup whereby buffer means may be utilized to assist in holding the deoxidizing means in place between the chamber and tubular means.

Another object of the invention is to provide a device with a deoxidizing means which is of such a character that it may be stated that it is substantially instantaneously gradually diffused by and into the metal flowing toward the primary chamber.

Also, an object is to provide a device of the character described which includes a sleeve, preferably square in cross-section, which surrounds the tubular means, a casing preferably square in cross-section, which surrounds the tubular formation and sleeve whereby to assist in holding the half sections and other components assembled, and a generally arch-shaped support has legs secured in a pair of corners of the sleeve in relation to the tubular means and a bridge joining the legs which serves to support the outer extremity of the tubular means adjacent to its entrance.

Additional specific objects of the invention reside in providing a device with a shield inset from the entrance of the tubular means, and deoxidizing means which is applied as a liner or layer to at least one of the passages communicating with the primary chamber.

A particular object is to provide half sections in which the tubular formation thereof is formed by a pair of what may be termed channel portions or extended portions provided with grooves, and these channel or extended portions are at least partially held together by tape means at their longitudinal meeting edges whereby to prevent the outflow of any molten metal therebetween.

A further object of the invention is to preferably form the extended or channel portions with internal mating surfaces which taper or generally converge toward the primary chamber to provide what may be termed an intermediate or mixing chamber located between the primary chamber and tubular means whereby to pilot or funnel the flow of metal into the primary chamber.

Another important object of the invention is to provide a device having the mating surfaces described in the preceding paragraph which are so tapered or shaped that they assist in locating the tubular means and deoxidizing means in relation to one another and said surfaces.

A further objective is to provide half sections which also include enlarged or recessed head portions in which the recesses form the primary chamber alluded to above, and the head portions preferably have relatively thick outer or end chordal portions which are provided with one or more pairs of mating grooves which cooperate to define one or more secondary chambers communicating with the primary chamber for receiving molten metal therefrom to obtain sample portions of a predetermined size and weight which are joined to a head portion formed in the primary chamber but are adapted for severance therefrom for analysis.

Another significant objective of the invention is to provide the extended or channel portions of the half sections with internal mating surfaces which define an entrance or passage which is interposed between the primary chamber and mixing chamber and communicates therewith.

An important object is to provide at least one device in which the cross-dimension of the entrance or passage described in the preceding paragraph is predetermined and the internal cross-dimension of the tubular means is also of a predetermined size in direct proportion or ratio to that of the passage.

A specific object is to provide a unique method of deoxidizing the sample obtained.

Additional objects and advantages of the invention reside in providing a device which is efficient, durable, comprised of a minimum number of components which can be economically manufactured and assembled on a production basis and which can be readily disassembled or broken apart after use to obtain a sample.

Reference is hereby made to my copending applications Ser. Nos.: 543,687 filed Jan. 24, 1975; 563,581 filed Mar. 31, 1975; 595,155 filed July 11, 1975; 656,660 filed Feb. 9, 1976; and 690,296 filed May 26, 1976 which disclose, among other things, a secondary chamber or chambers which are described and/or defined in various ways.

Other objects will become apparent after the description hereinafter set forth is considered in conjunction with the drawings annexed hereto:

In the drawings:

FIG. 1 is a partial view of a lance or wand provided with a connector for detachably supporting a device for receiving liquid, such as molten metal;

FIG. 2 is a sectional view of the device of FIG. 1, and depicts a mode of obtaining a sample of molten metal from a stream thereof;

FIG. 2a is one end view showing certain structural details of the device;

FIG. 3 is a longitudinal sectional view of a modified device for obtaining a sample of molten metal;

FIG. 4 is one end of the device shown in FIG. 3;

FIG. 5 is a longitudinal sectional view of a modified device;

FIG. 6 is one end view of the device shown in FIG. 5;

FIG. 7 is a pictorial view of a buffer means or deoxidizing means which is utilized in the devices of FIGS. 3 and 9;

FIG. 8 is a transverse section taken substantially on line 8 — 8 of FIG. 5;

FIG. 9 is a longitudinal section of a modified device;

FIG. 10 is a view of a sample obtained by utilizing the device of FIG. 9;

FIG. 11 is a perspective view of a modified device;

FIG. 12 is one end view of the device shown in FIG. 11, with a component of the device removed;

FIG. 13 is a longitudinal section taken substantially on line 13 — 13 of FIG. 11;

FIG. 14 is a transverse section taken substantially on line 14 – 14 of FIG. 13;

FIG. 15 is a pictorial view of a sample obtained by utilizing the device of FIG. 11;

FIG. 16 is a longitudinal section taken through a modified device;

FIG. 17 is a partial longitudinal sectional view of a modified device;

FIG. 18 is a partial section of structure constituting components of a modified device;

FIG. 19 is a partial section of a structure constituting components of a modified device; and FIG. 20 is a section of a portion of a modified device embodying a different form of deoxidizing means.

Referring to FIGS. 1, 2 and 2a there is disclosed a device generally designated 1, carried by a connector 2 on a lance or wand 3, for disposition in a stream of molten metal 4 for obtaining a sample therefrom for analysis.

The lance 3 may be constructed as desired but is preferably in the form of an elongated piece of pipe and the connector may also be made as desired, but is preferably in the form of an elongated generally tubular member having an open-ended extremity for receiving an end of the lance and an opposite extremity which is preferably provided with a bifurcation forming opposed pairs of marginal edges 6. The device 2 is elongated and includes, among other elements, to be subsequently described, an outer casing 7 which is adapted for reception in the bifurcation for intimate engagement with the marginal edges 6 for gripping and detachably holding the device to the connector in a position substantially transverse to its longitudinal axis, as well as the longitudinal axis of the lance, in order that an operator may present the device to the stream of molten metal as alluded to above.

The device generally designated 1 is preferably comprised of a pair of half sections generally designated 8, tubular means 9 and 9', buffer or deoxidizing means 10, a sleeve 11 and the casing 7.

The half sections 8 may be constructed of any material suitable for the purpose, such as molded powdered metal, and may be shaped as desired, but as shown, each section preferably includes a relatively large round head or enlarged portion 12 provided with a substantially round recess 13 which substantially forms an annular rim 14 provided with tapered mating projections and notches 15 which assist in correctly facilitating assembly of the sections and serve to provide side vents 16 for the escape of air when metal flows into the device.

Each half section is also formed to provide what may be termed an extended channel portion 17 or extended portion provided with an elongated longitudinal groove 18 and notch 19 adjacent to the recess 13. When the sections are correctly assembled with the projections and notches 15 in registry the recesses 13 will define a primary chamber 20 for receiving molten metal and the extended portions 17 will define a tubular formation which receives the tubular means 9'. More specifically, the longitudinal grooves 18 define an elongated cylindrical opening which receives the tubular means 9' and the notches 19 define a passage or entrance to the primary chamber 20 and abutment means 19' are provided for limiting inward movement of the tubular means 9'. It will be noted that the length of the tubular means 9' substantially corresponds to the length of the tubular formation and that the outer ends of this formation and means 9' are disposed in a flush relation.

The buffer means or deoxidizing means 10, above referred to, is preferably in the form of a disc or washer having an outside diameter which substantially corresponds to the outside cross-dimension of the tubular formation of the sections. The means 10 abuts the tubular formation and tubular means 9' and is provided with an opening 21 which provides communication between this tubular means and the tubular means 9. Attention is directd to the fact that the internal cross-dimension of the tubular formation and the outside cross-dimension of the tubular means 9' are preferably such that the tubular means is more or less clamped in place, between the channel portions when the casing 7 is telescoped about these portions and that the means 9' is held against longitudinal movement by the buffer means 10 and the abutment means 19' formed adjacent the notches. The buffer means preferably has a thickness of one eighth inch but its thickness and diameter may be greater or less than that shown.

The tubular means 9 has a length greater than that of the tubular means 9' and has an inner extremity which engages the buffer means 10 and an outer extremity provided with a bevelled snout or entrance 22 whereby to facilitate entry of molten metal when the snout is inserted at a correct angle into the stream 4. The means 9 may also be referred to as an entry tube or chamber.

The sleeve 11 is preferably of a length whereby its inner end engages the buffer means 10 and its outer end is flush with the outer end of the casing 7.

The device 1, if so desired may include a planar shield 23 of suitable size having an opening 24 therein through which the tubular means 9 extends in order that the shield may be held in abutting relationship with the ends of the sleeve and casing. Cement may be placed as indicated at 25 to assist in securing and stabilizing the position of the shield. This shield serves to protect the sleeve and casing, deflect molten metal away from the device, as well as protect an operator.

The structural characteristics of the components of the device are preferably such that they are substantially held in firm or snut frictional engagement with one another. The casing, sleeve and shield may be constructed of any material suitable for the purpose but are preferably made of pasteboard and the casing and sleeve are also preferably substantially square in cross-section, although they may be round in cross-section.

Attention is directed to the fact that the internal cross-dimension of the tubular means 9' is preferably equal to or greater than that of the opening 21 in the means 10 and that the inside cross-dimension of the tubular means 9 is preferably greater than that of the opening.

Attention is particularly directed to the important fact that the means 10 has been referred to as a buffer means and/or deoxidizing means. This terminology is employed because the means 10 can constitute or serve both as a buffer and as a deoxidizer, or it can be made to serve only as a buffer or as a deoxidizer. The means 10 is preferably made of aluminum for conditioning a metal, such as steel, and is diffused by and into the molten metal as it flows through the opening 21 but may be made of different material for other metals. However, if the means 10 is to be utilized only as a buffer then it will be constructed of a material which is highly resistant to heat, such as Pyrex, quartz or ceramic.

A sample obtained by utilizing the device 1 will comprise a head formed in the primary chamber 20, a relatively slender cylindrical portion formed in the tubular means 9', and a larger cylindrical portion formed in the tubular means 9 which is joined to the slender portion by a portion formed at the location of the means 10. The slender portion is joined to the head portion by an intermediate restricted or neck portion formed by the entrance or passage defined by the notches 19. With this setup the various portions of the sample may be served, as desired, for analysis.

Attention is directed to the fact that the casing 7 may be referred to as a grip or body member which is of a sufficient length for reception or accomodation in the bifurcation of the connector 2 at any one of an infinite number of positions along the casing and may be adjusted to any desired angular position with respect to the longitudinal axes of the connector and lance in order that an operator will have options with respect to an infinite number of standing positions and/or positions as to penetrating the molten metal stream.

FIGS. 3, 4 and 7 disclose a modified device generally designated 30 which preferably comprises a pair of half sections generally designated 31, a sleeve 32, entry tubular means 33, a casing 34 and a coiled deoxidizing means 35.

More particularly, the half sections 31 are similar to the half sections 8 described above and include head portions 36 having recesses 37 which define a primary chamber 38 and with thick chordal end portions 39 provided with axially extending tapered grooves 40 which define a tapered secondary chamber 41 for receiving molten metal from the primary chamber. The half sections also include a pair of extended channel portions or extended portions 42 respectively provided with elongated longitudinally extending grooves 43, relatively short grooves 44 and intermediate tapered grooves 45 which are located between and join the grooves 43 and 44 and converge toward the grooves 44. The grooves 44 define an entrance or passage 44' leading to the primary chamber and the tapered grooves define what may be termed a conical mixing, intermediate piloting or funnelling chamber or means 46 whereby to facilitate flow of the molten metal successively into the primary chamber 38 and secondary chamber 41. The chamber or means 46 is somewhat larger than the entrance 44'.

The extended or channel portions 42 constitute a tubular formation and an inner extremity of the tubular means 33 is held in an opening defined by the grooves 43 and engages an inner portion or coil of the deoxidizing means 35 for maintaining this inner portion of the coil against the converging tapered surfaces 45 or sides of the conical mixing chamber 46 for holding the means 35 in place with the major portion thereof being centered and extending forwardly in the tubular means 33. The sleeve 32 surrounds the tubular means 33 and has an inner end which abuts the outer ends of the extended portions 42 of the half sections and an outer end which is located in a flush position with the outer end of the casing 34. It should be noted that the outer extremity of the tubular means 33 extends but a relatively short distance beyond the outer ends of the sleeve and casing, is supported by the sleeve and casing, and is provided with a bevelled entrance 47 for disposition in a stream of molten metal.

The structural character of the deoxidizing means 35 is such that the molten metal flowing through the tubular means will substantially melt and diffuse the means 35 within the confines of the tubular means and/or in the mixing chamber 46 or entrance 44'. It may be stated that the deoxidizing means 35 is substantially instantaneously gradually melted in the tubular means, due to its shape and forward position therein. The means 35 shown is preferably in the form of a conical coil of strip stock or rectangular cross-section, but if desired, it may be in the form of a conical coil of wire of circular cross-section.

The half sections 31 may be of molded powdered metal like the sections of the device 1 or may be constructed of any other material suitable for the purpose as stated above.

The sleeve 32 and casing 34 may be constructed of any material suitable for the purpose but are preferably made from pasteboard and are square in cross-section.

The tubular means 33 is preferably made of Pyrex or other desirable inexpensive equivalent material as compared to quartz or other expensive material.

Attention is directed to the important fact that the tubular means 33 preferably has an inside cross-dimension or diameter of 8 mm.; that the entrance 44' has a cross-dimension or diameter of 6 mm.; and that the inner portion or largest coil of the deoxidizing means has a cross-dimension of 9 mm.; all for the purpose of providing an efficient flow of the molten metal into the primary chamber from the entrance 47 which initially receives the molten metal from the stream 4 or from some other source. It should be noted that the tapered or generally conical surfaces of the mixing chamber 46 may be considered to be cam means against which the inner portion of the deoxidizing means 35 is pressed or held by the tubular means 33. The chamber is of a sufficient size to promote diffusion of the means 35 therein and its conical character serves to promote or funnel the conditioned molten metal through the entrance 44' into the primary chamber 38.

Attention is further directed to the fact that the secondary chamber 41 is tapered outwardly. In other words, the chamber 41 has a larger inner cross-dimension leading to the primary chamber as compared to its outer cross-dimension, so as to insure a complete filling of the chamber 41 and obtain a sample of predetermined shape and particularly having a weight of substantially 1 gram, which may be readily severed from a head portion for analysis. More specifically, and as depicted in FIG. 3 one inner cross-dimension of the secondary chamber is preferably 0.215 inch and one outer cross-dimension is 0.210 inch. The primary chamber serves to form a head portion of a sample, the tubular means 33 a cylindrical stem portion, the tapered entrance 44' a relatively short cylindrical portion joined to the head, and a tapered portion formed in the conical chamber, which portion is joined to the short cylindrical portion and the larger cylindrical portion formed in the tubular means. Obviously, any of these portions of the sample may be utilized for analysis in accord with accepted standards utilized in the trade. The provision of vents like the vents in the device 1 serve to facilitate flow of the metal into the device.

Moreover, attention is directed to the fact that the diameter or cross-dimension of the entrance 44' may be varied, for example, within a range of 3.4 mm. to 6.5 mm. and that the internal cross-dimension or diameter of the tubular means may also be varied within a range of 6 mm. to 8 mm.

More particularly, tests have proven the desirability of such ranges to obtain a desirable flow of molten metal into the device and that it is preferable to maintain a predetermined differential ratio or value of 2 mms. within the ranges as above referred to, for example, if the cross-dimension or diameter of the entrance 44' is 4mm. then the cross-dimension or diameter of the tubular means 33 should be 6 mm., or the ratio can be 6 mm. to 8 mm. which has proven very satisfactory, as exemplified in FIG. 3.

FIGS. 5, 6 and 8 disclose another modified device generally designated 50. This device substantially corresponds to the structure embodiment in the device 30 except that a buffer means 51, similar to the buffer means 10 is utilized; that tape 52 is employed to close off an outer end of a secondary chamber 53; and that tapes 54 are used to seal or close off engaged longitudinal mating surfaces 55 of extended or channel portions 56 of a pair of half sections 57. More particularly, the device 50 comprises the half sections 57 which substantially correspond to the half sections 31 of the device 30, a tube 58 which is provided with a bevelled entrance, a sleeve 59, and a casing 60 which substantially respectively correspond to the tubular means, sleeve and casing of the device 30.

Attention is directed to the fact that the deoxidizing means 51 is held against a conical or cam surfaces 61 of a conical chamber 62 by the tube 58 and that the half sections are formed to provide a relatively short entrance or passage 62' which establishes communication between the conical chamber and a primary chamber formed by head portions of the half sections. The deoxidizing means is melted and diffused in the conical chamber 62 and/or passage 62' by the inflow of hot metal for substantially conditioning it prior to entry into the primary chamber.

The taper of the conical surface of the conical chamber 62 is such that tubes 58 of variable outside diameters may be used to engage such surface at different locations and also engage the means 51 and hold it against such surface. For example, if a tube engages the conical surface at a location at some point or location intermediate the length of the conical chamber, as shown, then a cylindrical space occurs between the outer cylindrical surface of the tube and the opening formed by the channel portions of the half sections, in which event, one of more wraps of tape or cement 63 may be placed about the extended channel portions of the sections to substantially fill such space or void. In some instances, the inner end of the tube may not engage the conical surface, in which event, the tape or cement will prevent or minimize any lateral flow of the molten metal between the mating surfaces of the half sections.

The tape 52 in addition to closing off the sectionary chamber 53 also serves to hold the head portions of the half section together and the tapes or cement 54 serve to hold the extended portions 56 of the sections together in addition to preventing any lateral outflow of any metal between the mating surfaces 55.

FIG. 9 illustrates a modified device generally designated 65 which substantially corresponds to the device 30 except for the half sections which include a pair of generally oblong head portions 66 (one shown) which respectively have thick curved end portions 67 provided with three speced corresponding tapered grooves 68 which cooperate to form three tapered secondary chambers for receiving molten metal from a primary chamber formed by the head portions. Obviously, the head portions may be provided with any number of grooves to obtain a desired number of secondary chambers.

The device 65 also includes a deoxidizing means 69, a tubular means 70, sleeve 71 and casing 72 which respectively substantially correspond to those of the device 30.

FIG. 10 depicts a face view of a sample generally designated 73, obtained by utilizing the device 65. More specifically, this sample includes an oblong head portion 74 formed in the primary chamber and three corresponding tapered portions 75 formed in the secondary chambers, a relatively short cylindrical portion 76 formed in an entrance leading to the primary chamber, a conical portion 77 formed in a conical chamber, and an elongated cylindrical stem portion 78 formed in the tubular means 70 and which has a diameter greater than that of the short portion 76. The secondary chambers are precisely formed so that the portions 75 when severed from the head for analysis will weigh 1 gram each.

A modified device generally designated 80 is exemplified in FIGS. 11 through 14 whereby to obtain a sample generally designated 81 as shown in FIG. 15. This device comprises a pair of half sections generally designated 82 an inner tubular means or tube 83' and an outer tubular means 83' of Pyrex or equivalent inexpensive material, an outer tubular casing 84, a sleeve 85, supporting means generally designated 86 and a planar shield 87. The half sections include recessed head portions 88 having integral chordal end portions 89 (one shown) provided with axially extending recesses 90 therein and with extended channel portions 91 having grooves 92 therein. The casing and sleeve and shield are preferably constructed from pasteboard and the casing and sleeve are preferably rectangular or square in cross-section. When the sections are correctly assembled the head portions define a primary chamber or cavity, the axial recesses 90 define what may be termed a secondary chamber or cavity 93 of predetermined size and configuration and the extended portions 91, and grooves 92 define a tubular formation.

The tubular means or tube 83' has an inner extremity which abuts a buffer means or element 94, preferably of aluminum, located between this extremity and the extended portions 91 or tubular formation of the half sections and an outer extremity provided with a bevelled entrance 95. The sleeve 85 surrounds the tube 83' and its inner end engages the buffer means 94 and its outer end is substantially flush with the outer end of the outer casing 84. This buffer means may be constructed of any material suitable for the purpose and may be termed a tubular element or washer having an opening 94' therein which has a diameter equivalent to or less than the inside diameter of the tube 83 so that there is flow and some interruption in this flow of molten metal from the tube 83' into the tube 83. This interruption serves to cause the molten metal to substantially instantaneously melt and diffuse the element 94 for deoxidizing the metal as it flows into the tube 83. This buffer means, as alluded to above, also serves to reduce the shock factor resulting from the inflow of hot metal. Various factors relative to different buffer means will be described subsequently.

The shield 87, above referred to, is provided with an opening 95 through which the tube 83' extends and cement 96 may be used to secure the shield to the casing and tube and the casing to the head portions of the half sections. Obviously, cement may be placed at locations other than those shown for securing the components together as a composite unit.

The supporting means 86, above referred to, and as shown in FIGS. 11, 13, and 14 is preferably generally arched or U-shaped and includes a pair of legs 97 and a bridge 98. The inner extremities of the legs are secured by cement or mastic 99, between the sleeve 85 and the tube 83', as shown in FIGS. 13 and 14, and so that portions of the legs extend outwardly from the outer ends of the sleeve and casing and along the outer extremity of the tube whereby at least the bridge 98 will be located adjacent the entrance 95 of the tube for supporting its outer extremity. More specifically, it should be noted that the inner extremities of the legs 97 are secured in opposed corners of the sleeve 85 and may more or less linearly engage the tube 83' throughout at least a portion of its length in order to provide generally parallel lines of support therefor, in addition to the support afforded by the bridge. The cement or mastic 99 is located in the corners of the sleeve and at least partially about the tube 83' and serves to hold the latter in the sleeve 85, in addition to securing the supporting means in the sleeve. The use of the tube 83' constructed of Pyrex or equivalent inexpensive material in combination with the supporting means serves to reduce the overall costs of manufacture as compared to a device which employs a tubular means made of quartz.

The device 80 is adapted for attachment to the lance 3 through the connector 2, for use in introducing and removing the entrance of the device with respect to the stream or mass of molten metal 4 and the shield 23 assists in protecting the casing and head portions of the half sections, including an operator, and in a manner as substantially described above.

When the device is utilized correctly, the sample 81 of the configuration depicted in FIG. 15 will be obtained. More particularly, the sample includes a head portion 100 formed in the primary chamber, a portion 101 formed in the secondary chamber 93, an extended portion 102 formed in the tube 83 in the half sections, an intermediate tapered portion 103 and a cylindrical stem portion 104 which is somewhat longer and larger in cross-section than the portion 102.

If so desired, a length of wire 105 may be utilized to facilitate identification of the sample 81 and/or the portion 101. This wire may be bent so that a loop portion, such as 106, can be disposed in the secondary chamber 93, as shown in FIGS. 13, or into the primary chamber, in order that metal flowing into chamber 93 from the primary chamber will automatically cause the portion 106 of the wire to become imbedded in the resulting metal sample. When the sample 81 is recovered, the portion 101, will have a size and a weight of preferably 1 gram which has been predetermined and can be readily severed from the head for analysis, in addition to the other portions thereof. The wire may be attached to a tag for identification purposes. A piece of tape 107 of suitable heat resistant material may be secured to the half sections as shown in FIG. 12, whereby to assist in securing them together and closing off the outer end of the secondary chamber 93 to prevent outflow of metal therefrom. Obviously, the tape is also used to secure the wire 105 in position.

FIG. 16 illustrates another modified device generally designated 110. This device includes a tubular means 111 of appreciable length and has an inner extremity secured in a tubular formation formed by channel portions 112 (one shown) of a pair of half sections 113, a sleeve 114 and an outer casing 115, both of which are preferably constructed of pasteboard and square of rectangular in cross-section. The sleeve 114 surrounds the tubular means or tube 111 and abuts the tubular formation and its outer end is flush with an end of the casing 115. Cement or mastic may be interposed between the tube and the sleeve to secure them together in a manner according to FIG. 14 and some of this cement as indicated at 116 may be applied to the outer ends of the sleeve and casing whereby to prevent entry of molten metal when an entrance end 117 of the tube 111 is introduced into a stream of molten metal. Due to the appreciable length of the casing and location of the sleeve the outer extremity of the tubular means is fairly well supported. The tube 111 is preferably constructed of Pyrex or equivalent inexpensive material.

FIG. 17 depicts a further modified device generally designated 120. This device comprises a pair of half sections having channel portions 121 (one shown) forming a tubular formation, a tubular means or tube 122 of Pyrex or equivalent inexpensive material, a sleeve 123 and a casing 124. The sleeve and casing are preferably made of pasteboard and square or rectangular in cross-section. It should be noted that the sleeve extends outwardly from the casing 124 and serves to support the extended portion or extremity of the tube 122. Cement 125 may serve to seal the outer end of the casing to the sleeve and the outer end of the sleeve to the tubular means. The device 120 affords a setup whereby the molten metal will flow directly into a cylindrical passage formed by the channel portions and this passage has a diameter somewhat less than the internal diameter of the tube 122. It should be further noted that the inner ends of the tubular means and sleeve abut the ends of the channel portions of the half sections.

Attention is directed to the important fact that the internal surfaces defining the passage or opening formed by the channel portions 121 of the sections are provided with a layer or coating 126 of means, such as aluminum or some other pyrophoric substance which is sprayed onto the surfaces to constitute an element for deoxidizing the metal flowing through the passage, as distinguished from the other forms of deoxidizing means described in the subject application. Obviously, a layer or coating of aluminum or equivalent material could be sprayed or otherwise applied to the inner surface of the tube 122, or to any of the tubes, passages or chambers located between an outer entrance and a primary chamber. For example, the internal surface of the tube 58, entrance 62' or chamber 62 shown in FIG. 5 could be provided with a layer of aluminum of sufficient thickness in lieu of the means 51, in which event, the inner end of the tube 58 would more or less only engage the conical surface or surfaces 61 of the chamber 62.

FIG. 18 discloses a partial section of a device in which a buffer means 130 preferably in the form of a washer of Pyrex glass or other heat resistant material is held between a tubular formation formed by a pair of channel portions 131 (one shown) of a pair of half sections and a tubular means or tube of Pyrex 132 or equivalent material. The buffer means 130 is provided with a center opening 133 providing communication between the tubular formation and the tubular means 132. The diameter of the opening is preferably less than the inside diameter of the tubular formation and the diameter of the latter is somewhat less than the inside diameter of the tubular means.

Attention is directed to the important fact that the buffer means serves to reduce the shock imparted to the internal components when a bevelled snout or entrance of the tube 132 is inserted into the stream 4 of molten metal.

Of particular significance is the fact that the buffer means 130 also serves to hold an end of an elongated flexible deoxidizing means or element 134 between the buffer means and the inner end of the tube 132 so that the remaining portion or extremity of the elemrnt 134 will extend rearwardly through the opening 133 into the tubular formation of the half sections. The buffer means also serves to hold an end of a second deoxidizing means or element 135 between the means 130 and the tubular formation so that the remainder or opposite extremity of the element 135 also extends rearwardly like the element 134 into the tubular formation. Obviously, the elements 134 and 135 may be identical of different.

In FIG. 19 there is disclosed a partial section of a device which substantially corresponds to the device shown in FIG. 18, except for the fact that a buffer means 136 of metal, such as aluminum, is utilized in lieu of the buffer means 130 so that the means 136 constitutes a buffer as well as a deoxidizing means, as distinguished from the non-metallic buffer means 130 above referred to. The device of FIG. 19 comprises substantially the same components shown in FIG. 18 and additional components to provide a complete device for use.

Referring to FIG. 20 there is disclosed a sectional view of a portion of a device generally designated 150 which embodies a modified deoxidizing means generally designated 151. More specifically in this regard, there is shown one of a pair of channel portions of a pair of half sections which when assembled provided a tubular formation or wall structure and a tubular means or tube 152 of Pyrex or equivalent or different material has an inner end disposed in relation to the outer end of the tubular formation and an outer extremity provided with a bevelled entrance. The deoxidizing means preferably includes a tubular cylindrical portion 153 and an annular radial flange 154, the latter of which is interposed or held between the ends of the tubular formation and tube so that the cylindrical portion extends forwardly in the tube for melting and diffusion by and into the molten metal for conditioning the latter. It should be noted that the internal cross-dimension of the deoxidizing means is preferably somewhat greater than the internal cross-dimension of the opening or passage of the tubular formation; that a casing surrounds the channel portions of the half sections; and that a sleeve surrounds the tube and is interposed between the tube and the casing for holding the component assembled in a mode substantially corresponding to the assembly depicted in FIG. 13.

It is to be distinctly understood that the internal cross-dimensions of the various outer or inlet tubular means, inner tubular means, chambers and openings in the extended portion of the half sections, or entrances or passages between the inlet of the outer tubular means and the primary chamber may be varied as desired. Otherwise expressed, the cross-dimensions may have configurations which are square, rectangular, triangular, oval, or otherwise, provided there is a predetermined volumetric relationship between the inlet and primary chamber of the device. This relationship, including the ratio factor above referred to, is particularly desirable in those devices disclosed herein in which the metal flows through passages of variable internal diameters prior to entering the primary chamber.

Having thus described my invention or inventions, it is obvious that various modifications may be made in the same without departing from the spirit of the invention and, therefore, I do not wish to be understood as limiting myself to the exact forms, constructions, arrangements, and combinations of the parts herein shown and described.

I claim:

1. A device of the character described for obtaining a sample of molten metal, said device comprising structure provided with an unevacuated chamber and an integral tubular formation extending therefrom, a tube disposed in axial relation to said tubular formation for initially receiving molten metal for flow into said chamber, buffer means held against a portion of said tubular formation by an inner end of said tube, and tubular means embracing at least a portion of said tubular formation for holding the components assembled.

2. The device defined in claim 1, in which said holding means includes a sleeve disposed about said tube, a casing is disposed about said sleeve and said tubular formation, and said sleeve and casing are non-circular in cross-section.

3. The device defined in claim 1, including a second tube disposed in said tubular formation in axial alignment with said first-mentioned tube, and said buffer means is also interposed between said tubes.

4. The device defined in claim 1, in which said structure is also provided with a smaller chamber which receives molten metal from said first-mentioned chamber.

5. Elongated structure for use in a device for obtaining a sample of molten metal from a supply thereof, said structure comprising a pair of axially disposed tubular means through which the metal flows, buffer means held against a portion of one tubular means by an inner end of the other for deoxidizing the metal as it flows from the other into the one, and a tube surrounding at least a portion of said structure for holding said tubular means assembled and affording a grip by a lance for disposing the structure transverse to the longitudinal axis of the lance.

6. Structure for use in a device for obtaining a sample of molten metal from a supply thereof, said structure comprising an inlet tube for initially receiving metal from the supply and a tubular means axially aligned with said inlet tube for receiving metal therefrom, said inlet tube having an internal cross-dimension greater than an internal cross-dimension of said tubular means, and buffer means held in relation to a portion of said tubular means by an inner end of said inlet tube.

7. The structure defined in claim 6, in which said buffer means is generally in the form of a disc which has an internal cross-dimension less than that of said second tube.

8. A device for obtaining a sample of molten metal, said device comprising a pair of half sections having head portions forming a chamber and wall structure forming a tubular formation, tubular means having an inner extremity disposed in said tubular formation and an outer extremity provided with an entrance for initially receiving molten metal for flow through said tubular means into said chamber, said wall structure also defining a passage between said chamber and tubular means, said passage having an internal cross-dimension of substantially 6 mm., and said tubular means having an internal cross-dimension of substantially 8 mm.

9. A device for obtaining a sample of molten metal, said device comprising a pair of half sections having head portions forming a primary chamber and wall structure forming a tubular formation, tubular means having an inner extremity disposed in said tubular formation and an outer extremity provided with an entrance for initially receiving molten metal for flow through said tubular means into said chamber, said wall structure also defining a passage establishing communication between said primary chamber and an intermediate chamber between and communicatively connected to said passage and tubular means, a preformed sleeve surrounding said tubular means, and a casing substantially surrounding and engaging said tubular formation and said sleeve, with said tubular means being centered in said sleeve.

10. A device for obtaining a sample of molten metal, said device being elongated and comprising structure forming an unevacuated chamber and structure forming tubular means extending therefrom provided with an entrance for introduction in molten metal so that a portion thereof will flow into said chamber, said structure having axially spaced portions, deoxidizing means interposed between said portions, and a tubular casing for holding the aforesaid structure assembled and affording connection with a lance at a location between said chamber and entrance.

11. A device for obtaining a sample of molten metal, said device comprising wall structure forming an unevacuated chamber and a tubular formation extending therefrom, tubular means having an inner extremity and an outer extremity provided with an entrance for introduction into molten metal whereby a portion thereof will flow into said chamber via said tubular formation and tubular means, deoxidizing means interposed and held between said inner extremity of said tubular means and a portion of said tubular formation, and a tubular casing for holding said wall structure and tubular means assembled and affording connection with a lance at a location intermediate said chamber and extension.

12. Means for use in a chambered device for obtaining a sample of molten metal, said means comprising a pair of tubular structures, means interposed and held between portions of said structures and extending into one structure for conditioning molten metal when it flows through said one structure into a chamber from the other structure, and means for maintaining said structures and interposed means assembled.

13. A subassembly comprising wall structure forming a chamber and a passage leading to said chamber, tubular means having an inner end secured in relation to said passage and an outer end having an entrance for initially receiving molten metal for flow into said chamber through said passage, and said passage having a cross-dimension within a range of between 3.4 mm. to 6 mm. and said tubular means having an internal cross-dimension within a range of between 6 mm. to 8 mm.

14. A subassembly comprising wall structure forming a chamber and a passage leading to said chamber, tubular means having an inner and secured in relation to said passage and an outer end having an entrance for initially receiving molten metal for flow into said chamber through said passage, an elongated deoxidizing means having an end secured in relation to a portion of said wall structure by an inner end of said tubular means and an opposite extremity extending forwardly in said tubular means toward said entrance.

15. A subassembly for the purpose described comprising wall structure forming a primary chamber for receiving a sample of molten metal and a smaller chamber constituting an entrance to said primary chamber, said smaller chamber being tapered generally toward said primary chamber whereby to facilitate flow of the metal into the primary chamber and tubular means having an inner end disposed in flow relationship with said smaller chamber and an outer end for receiving molten metal.

16. A subassembly for use in a molten metal sampling device for conditioning the sample, said subassembly comprising tubular means having a normally open entrance for initially receiving molten metal for flow longitudinally therethrough, and a conical coil of metal having at least a portion thereof in said tubular means which extends toward its entrance.

17. A device for obtaining a sample of molten metal, said device comprising wall structure forming a chamber and an entrance area tapered in a direction toward said chamber and communicating therewith, buffer means disposed in said area, and tubular means having an inner end disposed in relation to said area for holding said buffer means in place and an outer extremity provided with an inlet for initially receiving molten metal for flow into said chamber via said tubular means and said area.

18. The device defined in claim 17, in which said buffer means also comstitutes a deoxidizing means.

19. The device defined in claim 17, in which said buffer means is generally conical in shape and has an inner portion which is held in place by said tubular means and an outer portion which extends forwardly in said tubular means toward said inlet.

20. The device defined in claim 17, in which said tapered area affords a setup whereby anyone of a number of tubular means having variable cross-section dimensions may be disposed in relation to said area.

21. A device for obtaining a sample of molten metal, said device comprising structure forming a chamber and tubular means extending from said chamber and provided with an entrance for initially receiving molten metal for flow into said chamber, elongated deoxidizing means extending forwardly in said tubular means toward said entrance, and said structure and tubular means each having portions abuting a portion of said deoxidizing means for holding the latter in place.

* * * * *